(12) United States Patent
Murray et al.

(10) Patent No.: US 12,102,335 B2
(45) Date of Patent: Oct. 1, 2024

(54) RELOADABLE CLIP WITH A FLARING CAPSULE DEFORMATION

(71) Applicant: BOSTON SCIENTIFIC SCIMED, INC., Maple Grove, MN (US)

(72) Inventors: Collin Murray, Bolton, MA (US); Henry Stock, Sanbornton, NH (US); Laurie A. Lehtinen, Boylston, MA (US); Caitlyn Bintz Ashton, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/065,495

(22) Filed: Dec. 13, 2022

(65) Prior Publication Data

US 2023/0112714 A1    Apr. 13, 2023

Related U.S. Application Data

(63) Continuation of application No. 16/905,308, filed on Jun. 18, 2020, now Pat. No. 11,547,422.

(60) Provisional application No. 62/874,679, filed on Jul. 16, 2019.

(51) Int. Cl.
*A61B 17/128* (2006.01)
*A61B 17/122* (2006.01)
*A61B 17/00* (2006.01)

(52) U.S. Cl.
CPC ........ *A61B 17/1285* (2013.01); *A61B 17/122* (2013.01); *A61B 2017/0034* (2013.01); *A61B 2017/00818* (2013.01)

(58) Field of Classification Search
CPC ............ A61B 17/32056; A61B 17/221; A61B 2017/2212; A61B 2017/00738
See application file for complete search history.

(56) References Cited

U.S. PATENT DOCUMENTS

| 2002/0045909 | A1 | 4/2002 | Kimura et al. |
| 2007/0112359 | A1 | 5/2007 | Kimura et al. |
| 2017/0104475 | A1 | 4/2017 | Lam |

(Continued)

FOREIGN PATENT DOCUMENTS

| CN | 101810500 | 8/2010 |
| CN | 102274061 A | 12/2011 |
| CN | 103584898 A | 2/2014 |

(Continued)

*Primary Examiner* — Brooke Labranche
(74) *Attorney, Agent, or Firm* — Fay Kaplun & Marcin, LLP (57) ABSTRACT

A clipping system includes a clip having a pair of clip arms, proximal ends of the clip arms slidably received within a channel of a capsule to be moved between an open configuration and a closed configuration. A proximal end of the capsule including connecting tabs extending proximally therefrom. An applicator includes an elongated flexible member and a control member extending therethrough. The control member includes a distal end connected to the clip arms to move the clip assembly between the open and closed configurations. A distal end of the elongated flexible member includes a bushing including a first ramped surface, along which the connecting tabs slide along to engage a corresponding engaging feature of the bushing, and a second ramped surface proximal of the first ramped surface, the connecting tabs slidable along the second ramped surface to plastically deform toward a deployed configuration.

18 Claims, 5 Drawing Sheets

(56) References Cited

U.S. PATENT DOCUMENTS

2018/0153552 A1 6/2018 King et al.
2020/0205836 A1 7/2020 Uesaka et al.

FOREIGN PATENT DOCUMENTS

| JP | 2002-191609 | 7/2002 |
| JP | 2006-198388 | 8/2006 |
| WO | 2004/017839 | 3/2004 |
| WO | 2017/104475 | 6/2017 |

RELOADABLE CLIP WITH A FLARING CAPSULE DEFORMATION

PRIORITY CLAIM

The present application is a Continuation of U.S. patent application Ser. No. 16/905,308 filed Jun. 18, 2020; which claims priority to U.S. Provisional Patent Application Ser. No. 62/874,679 filed Jul. 16, 2019. The disclosures of the above application(s)/patent(s) are incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract, or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be used.

SUMMARY

The present disclosure is directed to a reloadable clipping system for treating tissue, comprising a clip including a pair of clip arms, each of the clip arms extending from a proximal end to a distal end, proximal ends of the clip arms slidably received within a channel of a capsule to be moved between an open configuration and a closed configuration. A proximal end of the capsule includes a plurality of connecting tabs extending proximally therefrom. An applicator includes an elongated flexible member and a control member extending therethrough, the control member including a distal end configured to be connected to the clip arms to move the clip assembly between the open configuration and the closed configuration. A distal end of the elongated flexible member includes a bushing including a first ramped surface, along which the connecting tabs slide along until engaging features of the connecting tabs engage a corresponding engaging feature of the bushing, and a second ramped surface proximal of the first ramped surface, the connecting tabs slidable along the second ramped surface to plastically deform toward a deployed configuration in which the connecting tabs are moved away from a longitudinal axis of the capsule to release the bushing therefrom.

In one embodiment, the corresponding engaging feature of the bushing may be a notch extending about a periphery of the bushing between the first and second ramped surfaces so that the notch defines a proximal end of the first ramped surface and a distal end of the second ramped surface.

In one embodiment, a diameter of the bushing at the proximal end of the first ramped surface may be greater than a diameter of the bushing at the distal end of the second ramped surface.

In one embodiment, the connecting tabs may be elastically deformable as the connecting tabs are slid along the first ramped surface so that, when the engaging features are positioned about the notch, the connecting tabs revert to their initial configuration and the engaging features are received within the notch to couple the capsule to the bushing.

In one embodiment, each of the first and second ramped surfaces may define conically shaped portions of the bushing which taper toward a distal end thereof.

In one embodiment, the engaging features of the connecting tabs may include an engaging element extending radially inward from a proximal end of each of the connecting tabs.

In one embodiment, the engaging element of each of the connecting tabs may extend substantially perpendicular relative to a longitudinal axis of the capsule.

In one embodiment, the engaging features of the connecting tabs may include a stamped boss extending inward, toward the longitudinal axis of the capsule.

In one embodiment, the proximal ends of the clip arms may be connected to one another via a yoke coupleable with an enlarged distal end of the control member.

In one embodiment, the yoke may include a proximal portion and a distal portion connected to one another at a point configured to separate when a predetermined force is exerted thereon.

The present disclosure also relates to a clip device, comprising a pair of clip arms, each of the clip arms extending from a proximal end to a distal end and a capsule extending longitudinally from a proximal end to a distal end and including a channel extending therethrough so that proximal ends of the clip arms are slidably received within the channel to be moved between an open configuration and a closed. A plurality of connecting tabs extend proximally from the proximal end of the capsule, each of the connecting tabs including an engaging feature extending therefrom toward a longitudinal axis of the capsule to engage a notch extending about a periphery of a bushing of an applicator. The connecting tabs are movable from an initial configuration toward a deployed configuration, in which the connecting tabs are plastically deformed in a direction away from the longitudinal axis of capsule to release the bushing therefrom.

In one embodiment, the engaging features of the connecting tabs may include an engaging element extending radially inward from a proximal end of each of the connecting tabs substantially perpendicular to the longitudinal axis of the capsule.

In one embodiment, the engaging features of the connecting tabs may include a stamped boss.

In one embodiment, each of the connecting tabs may include a window extending therethrough.

In one embodiment, the proximal ends of the clip arms may be connected to one another via a yoke coupleable with an enlarged distal end of the control member.

The present disclosure also relates to a method for treating tissue using a reloadable clipping system. A clip is loaded on an applicator by coupling a control member of the applicator to clip arms of the clip and by inserting a bushing distally into a proximal end of a capsule so that connecting tabs at the proximal end of the capsule slide along a first ramped surface along the bushing until engaging features of the connecting tabs engage a corresponding engaging feature of the bushing. The loaded clip assembly is inserted to a target site within a living body via a working channel of an endoscope. The clip is moved between an open configuration, in which distal ends of the clip arms are separated from one another, and a closed configuration, in which distal ends of the clip arms are moved toward one another, by moving the control member longitudinally relative to the catheter until target tissue is gripped therebetween. The clip arms are locked relative to the capsule in the closed configuration. The clip assembly is deployed from the applicator by drawing the control member proximally relative to the clip arms, until the connector tabs slide proximally along a second ramped surface of the bushing, plastically deforming the connector tabs from an initial configuration toward a deployed configuration in which the connector tabs are moved in a direction away from a longitudinal axis of the capsule to release the bushing therefrom.

In an embodiment, the corresponding engaging feature of the bushing is a notch extending about a periphery of the bushing between the first and second ramped surfaces so that the notch defines a proximal end of the first ramped surface and a distal end of the second ramped surface In one embodiment, the engaging features of the connecting tabs include engaging elements extending radially inward from proximal ends of the connecting tabs so that the engaging elements are received within the notch.

In one embodiment, during deployment, the distal end of the second ramped surface exerts a distal force on the engaging elements, bending each of the engaging elements against a corresponding one of the connecting tabs to be slid along the second ramped surface.

In one embodiment, the engaging features of the connecting tabs include a stamped boss extending along each of the connecting tabs to be received within a correspondingly sized and shaped notch extending about a periphery of the bushing.

BRIEF DESCRIPTION

DETAILED DESCRIPTION

The present disclosure may be further understood with reference to the following description and the appended drawings, wherein like elements are referred to with the same reference numerals. The present disclosure relates to a clipping system and, in particular, relates to a reloadable endoscopic clipping system, in which a clip may be loaded onto a distal end of an applicator prior to an endoscopic procedure. Once a clip has been deployed at a desired target area in the body, the applicator assembly may be reloaded with a new clip. Although shed parts (e.g., parts that are left in a body upon deployment of the clip) will pass naturally from the body under normal circumstances, shed parts may become trapped in larger defects after closure.

Exemplary embodiments of the present disclosure comprise a clip including clip arms slidable within a capsule to move between an open configuration and a closed configuration to clip tissue, as desired. A proximal end of the capsule includes connecting tabs facilitating a direct releasable connection of the clip with the applicator, which minimizes or eliminates a potential for shed parts in the body upon deployment of the clip. It will be understood by those of skill in the art that the terms proximal and distal as used herein, are intended to refer to a direction toward and away from, respectively, a user of the device.

As shown in FIGS. 1-9, a reloadable clipping system 100 comprises a clip 102 configured to be loaded onto an applicator 104 prior to insertion of the system 100 into a body to clip target tissue therein. The clip 102 includes a pair of clip arms 106, proximal ends 110 of which are slidably received within a capsule 108 so that the clip arms 106 may move between an open configuration, in which distal ends 112 of the clip arms 104 are separated from one another, and a closed configuration, in which distal ends 112 are drawn toward one another to grip tissue. A proximal end 114 of the capsule 108 includes a plurality of connecting tabs 116 extending proximally therefrom and configured so that, when, for example, a bushing 118 of the applicator 104 is inserted into the proximal end 114 of the capsule 108, the connecting tabs 116 engage a corresponding portion of the bushing 118 to couple the clip 102 to the applicator 104. Upon coupling of the bushing 118 to the capsule 108, an enlarged distal end 122 of a control member 120 of the applicator 104 is coupled to the clip arms 106 so that longitudinal movement of the control member 120 relative to the capsule 108 moves the clip 102 between the open and closed configurations.

As will be described in further detail below, once the target tissue has been clipped, as desired, a user (e.g., physician) of the system 100 initiates a deployment process which causes the connecting tabs 116 to plastically deform away from a centerline of the capsule 108 so that the bushing 118 is released therefrom. Since the connecting tabs 116 are plastically deformed without fracture to release the bushing 118, deployment of the clip 102 does not result in shed parts left in the body. The applicator 104 is configured so that, after deployment of the clip 102 in the body, a new clip 102 may be loaded onto the applicator 104 so that the same applicator 104 may be used to deliver the new clip 102 to a second portion of target tissue in the body. Each clip 102 according to this embodiment is stored in a cartridge 124, which facilitates loading of the clip assembly 102 onto the applicator 104.

Figure 1:
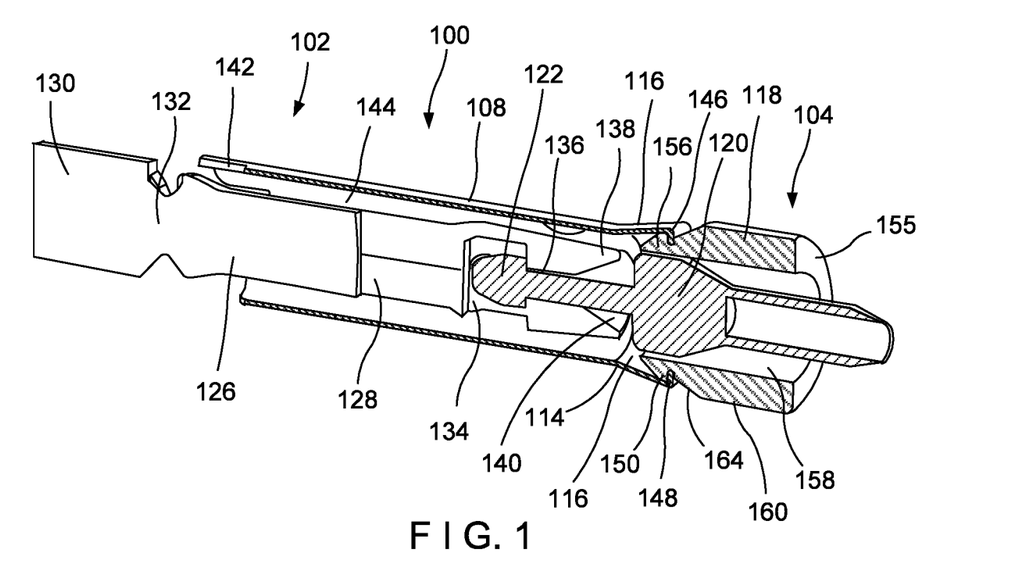
FIG. 1 shows a longitudinal cross-sectional view of a portion of a clipping system according to an exemplary embodiment of the present disclosure.
Figure 2:
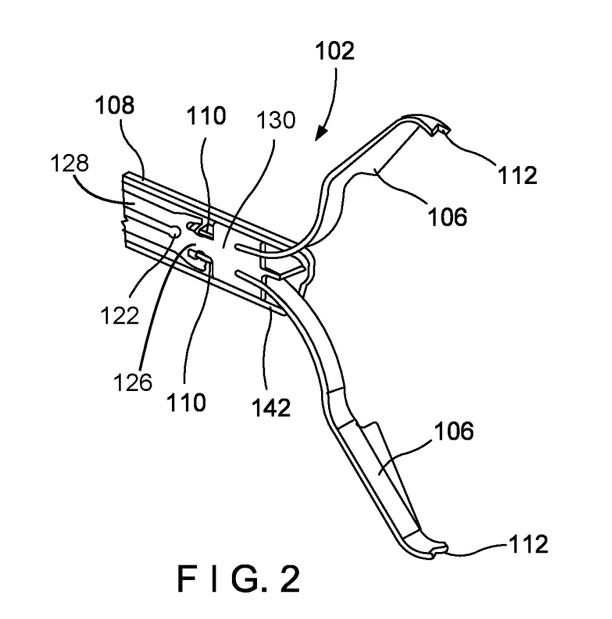
FIG. 2 shows another longitudinal cross-sectional view of a distal portion of a clip according to the system of FIG. 1.

As shown in FIGS. 1-2, the clip 102 includes the pair of clip arms 106, proximal ends 110 of which are, in this embodiment, connected to one another via a yoke 126 slidably received within the capsule 108. In this embodiment, the clip arms 106 are biased toward the open configuration so that, when not constrained by the capsule 108, the clip arms 106 move under their natural bias to the open configuration in which the distal ends 112 of the clip arms 106 spread apart from one another to receive tissue therebetween. In some embodiments, the clip arms 106 may be biased in a closed configuration. When the clip arms 106 are drawn into the capsule 108, the capsule 108 constrains the clip arms 106, holding the distal ends 112 together so that tissue may be gripped therebetween. The yoke 126 is longitudinally slidable within the capsule 108 to move the clip arms 106 proximally and distally relative to the capsule 108 between the open and closed configurations.

Each of the clip arms 106 extends from the proximal end 110, connected to the yoke 126, to the distal end 112. The distal ends 112 of one or both of the clip arms 106 may include tips extending laterally inward toward the other clip arm 106 with the tips including, for example, teeth, protrusions, spikes or other structures) configured to grip tissue between the distal ends 112. One or both of the clip arms 106 may also include a locking feature configured to lock the clip arms 106 in the tissue gripping configuration after target tissue has been gripped as desired by the clip arms 106. In one embodiment, one or both of the clip arms 106 includes a locking tab extending laterally outward therefrom configured to engage a portion of the capsule 108 when the clip arms 106 have been drawn into the capsule 108 by a predetermined distance. For example, the locking tabs may be received within correspondingly sized, shaped and positioned locking windows extending laterally into or through a wall of the capsule 108 to lock the clip arms 106 relative to the capsule 108, in the tissue gripping configuration.

The yoke 126 is connected to the proximal ends 110 of the clip arms 106 and is configured to be connected to the enlarged distal end 122 of the control member 120. In this embodiment, the yoke 126 includes a proximal portion 128 and a distal portion 130 connected to one another at a point 132 configured to break or separate when subject to a force exceeding a predetermined threshold value. For example, the point 132 may include a welding, a decreased diameter portion, or an adhesive that breaks or otherwise uncouples when sufficient force is exerted thereon. The distal portion 130 is configured to engage proximal portions of the clip arms 106 via, for example, a pair of protrusions extending therefrom and received within correspondingly sized and shaped openings extending through proximal portions of the clip arms 106 so that the clip arms 106 are held in position relative to one another.

The proximal portion 128 is configured to engage the enlarged distal end 122 of the control member 120. In one embodiment, the proximal portion 128 includes a cavity 134 sized and shaped to receive the enlarged distal end 122 and a longitudinal slot 136 extending proximally from the cavity 134 to a proximal end 138 of the yoke 126. The longitudinal slot 136 is sized and shaped to receive a portion of the control member 120 extending proximally from the enlarged distal end 122. In one embodiment, an opening of the longitudinal slot 136 at the proximal end 138 includes an angled surface 140 tapering toward a distal end thereof to facilitate insertion of the enlarged distal end 122 distally through the longitudinal slot 136 and into the cavity 134 during loading the clip 102 onto the applicator 104. The cavity 134 and the longitudinal slot 136 are configured so that, once the enlarged distal end 122 is received within the cavity 134, the enlarged distal end 122 is prevented from being proximally withdrawn therefrom. Thus, longitudinal movement of the control member 120 relative to the capsule 108 moves the clip arms 106 between the open and the closed configurations.

The capsule 108 extends longitudinally from the proximal end 114 to a distal end 142 and includes a channel 144 extending longitudinally therethrough. The channel 144 is sized and shaped to slidably receive the yoke 126 and the clip arms 106 therein. As described above, the capsule 108 of this embodiment also includes locking structures (e.g., locking windows) for engaging corresponding locking features (e.g., locking tabs) of the clip arms 106. The capsule 108 includes the connecting tabs 116 which, in an initial configuration, extend proximally from the proximal end 114 about a periphery of the proximal end 114, flaring radially outwardly therefrom. In particular, each of the connecting tabs 116 extends at an angle relative to a longitudinal axis of the capsule 108 such that a proximal end 146 of each of the connecting tabs 116 extends away from the longitudinal axis to form a substantially flared end.

The proximal end 146 of each of the connecting tabs 116 additionally includes an engaging element 148 extending laterally therefrom toward the longitudinal axis of the capsule 108. In one embodiment, the engaging element 148 extends substantially perpendicularly to the longitudinal axis. As will be described in further detail below, the engaging element 148 is configured to engage a corresponding notch or recess 150 of the bushing 118 of the applicator 104. In one embodiment, the capsule 108 includes four connecting tabs 116. It will be understood by those of skill in the art that the capsule 108 may include any number of connecting tabs 116 so long as the connecting tabs 116 are configured to engage the bushing 118, as described below.

Figure 3:
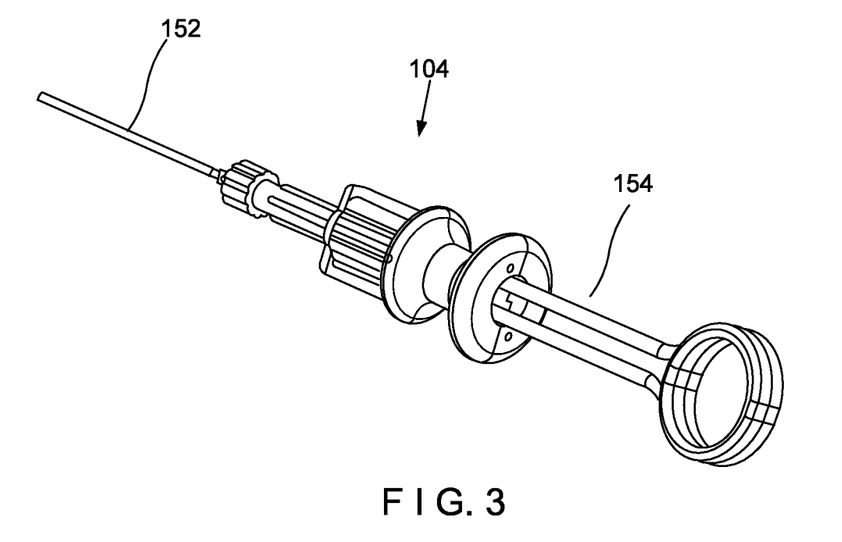
FIG. 3 shows a perspective view of an applicator according to the system of FIG. 1.

As shown in FIG. 3, the applicator 104 includes a flexible member 152 such as, for example, a catheter extending from a proximal end connected to a handle portion 154 that remains outside of the body during the clipping of target tissue, to a distal end including, for example, the bushing 118 for connecting the applicator 104 to the clip 102. The control member 120 extends through the flexible member 152, a proximal end of the control member 120 connected to the handle portion 154, which includes actuators for controlling a movement of the clip 102 once the clip 102 has been loaded onto the applicator 104.

In this embodiment, the bushing 118 is connected to the distal end of the flexible member 152 and is configured to be connected to the clip 102 via the connecting tabs 116 of the capsule 108. The bushing 118 extends from a proximal end 155 to a distal end 156 and includes a channel 158 extending therethrough. The proximal end 155 is connected to the distal end of the flexible member 152 while the distal end 156 is configured to engage the connecting tabs 116. When the bushing 118 is coupled to the capsule 108, the channel 158 of the bushing 118 is substantially aligned with the channel 144 of the capsule 108.

Figure 4:
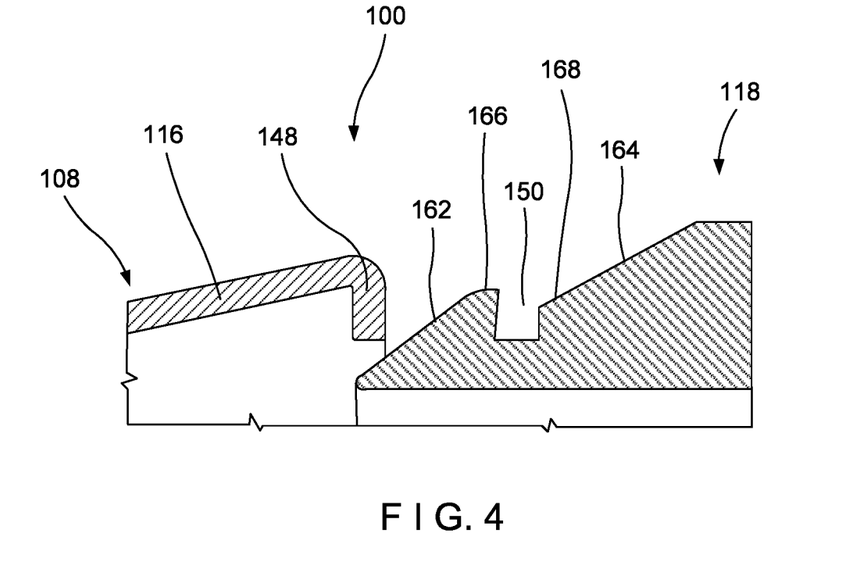
FIG. 4 shows an enlarged longitudinal cross-sectional view of a capsule and a bushing prior to engagement according to the system of FIG. 1.

An exterior surface 160 along a distal portion of the bushing 118 includes a first ramped surface 162 facilitating engagement of the distal portion of the bushing 118 with the flared end of the capsule 108 formed via the connecting tabs 116 at the proximal end 114 thereof and a second ramped surface 164 facilitating separation of the capsule 108 from the bushing 118 during deployment of the clip 102. The first and second ramped surfaces 162, 164 extend about a periphery of the bushing 118 to, in one embodiment, define substantially conical portions of the bushing 118. The notch 150 extends about a periphery of the bushing 118 between the first and second ramped surfaces 162, 164 so that the notch 150 defines a proximal end 166 of the first ramped surface 162 and a distal end 168 of the second ramped surface 164. The notch 150 is sized and shaped to correspond to a size and shape of the engaging elements 148 of the connecting tabs 116.

Figure 5:
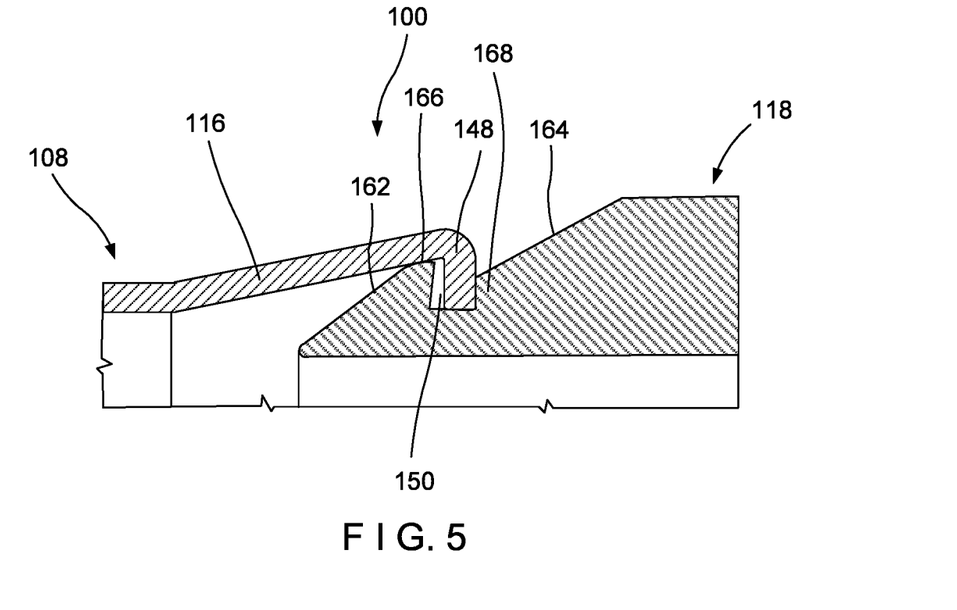
FIG. 5 shows an enlarged longitudinal cross-sectional view of the capsule and the bushing engaged according to the system of FIG. 1.

The first ramped surface 162 tapers toward the distal end 156 to facilitate insertion of the bushing 118 into the flared end formed via the connecting tabs 116 at the proximal end of the capsule 108. In particular, as the capsule 108 is drawn proximally over the bushing 118, as shown in FIG. 4, the connecting tabs 116 elastically deform (e.g., expand radially outward) as the engaging element 148 of each of the connecting tabs 116 slide along the first ramped surface 162. When the engaging elements 148 are positioned about the notch 150, the connecting tabs 116 revert to their initial configuration (e.g., the notch 150 allows the elements 148 to flex radially inward due to their natural bias) so that the engaging elements 148 are received within the notch 150, as shown in FIG. 5, and the capsule 108 is snapped over the bushing 118 via the connecting tabs 116. Once the engaging elements 148 are received within and engage the notch 150, the clip 102 remains coupled to the bushing 104 until deployment.

The second ramped surface 164 tapers toward the distal end 168 thereof. In one embodiment, a diameter of the bushing 118 at the distal end 168 of the second ramped surface 164 is smaller than a diameter of the bushing 118 at the proximal end 166 of the first ramped surface 162. As will be described in further detail below, when the clip 102 has been clipped over the target tissue, as desired, the control member 120 may be drawn proximally with respect to the capsule 108 until the clip arms 106 are locked relative to the capsule 108 (e.g., via locking tabs of the clip arms 106 received within locking windows of the capsule 108) in the closed configuration.

Figure 6:
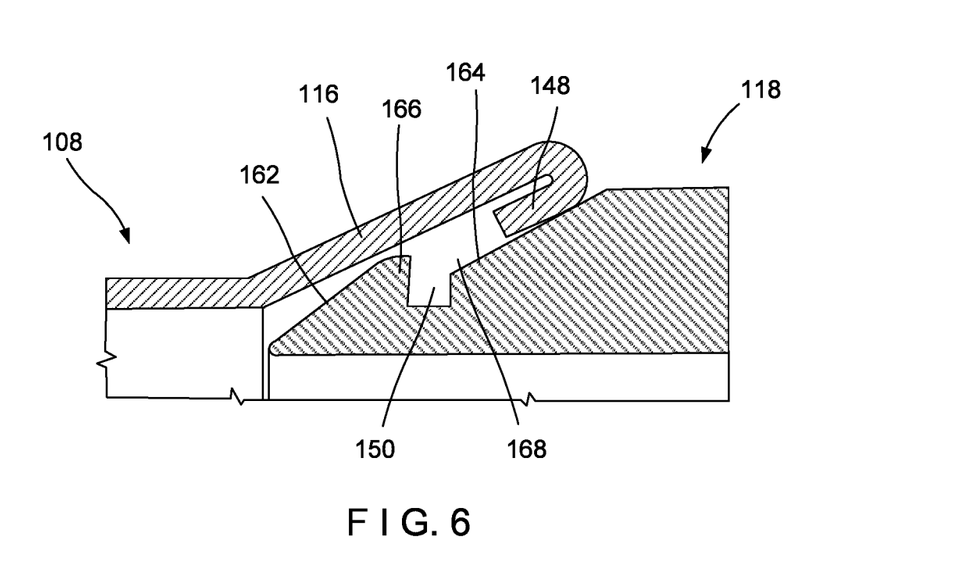
FIG. 6 shows an enlarged longitudinal cross-sectional view of the capsule and the bushing during an initial deployment stage according to the system of FIG. 1.
Figure 7:
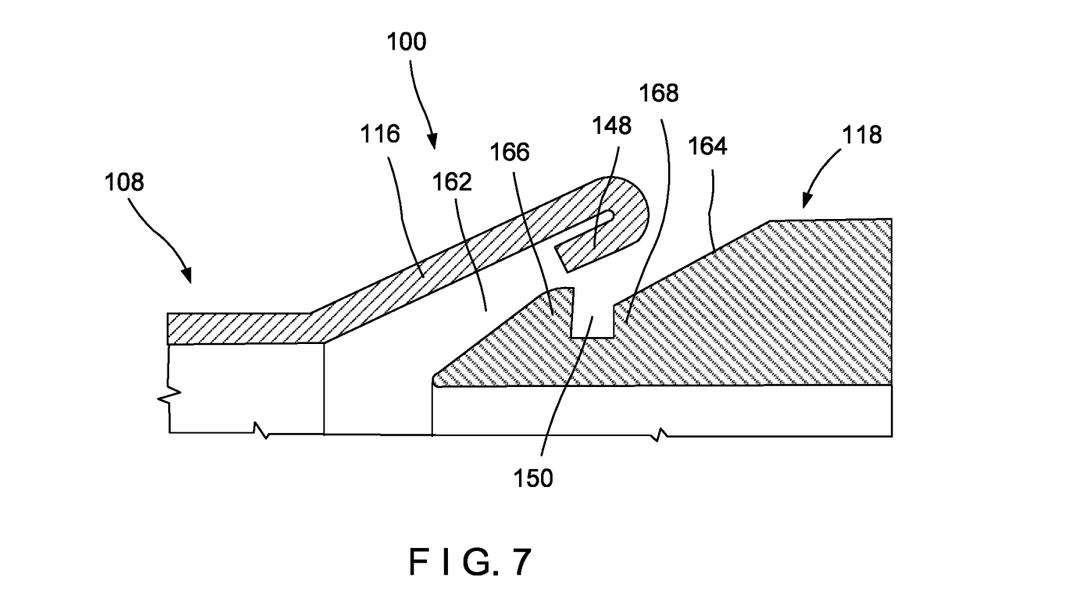
FIG. 7 shows an enlarged longitudinal cross-sectional view of the capsule and the bushing upon release of the bushing from the capsule according to the system of FIG. 1.

Further proximal movement of the control member 120 after this point draws the capsule 108 proximally against the bushing 118, as shown in FIG. 6, so that, when sufficient proximal force is applied, the engagement elements 148 are bent against the connecting tabs 116 and slid proximally along the second ramped surface 164. As the connecting tabs 116 are slid proximally along the second ramped surface 164, the proximal ends 146 of the connecting tabs 116 move further away from the longitudinal axis of the capsule 108, toward a deployed configuration in which an angle of the connecting tabs 116 relative to the longitudinal axis is increased to an extent that they are plastically deformed in this radially outwardly flared shape. In other words, as shown in FIG. 7, the connecting tabs 116 are permanently deformed radially outward so that the bushing 118 may be disengaged and removed from the capsule 108 without leaving any shed parts in the body.

Figure 8:
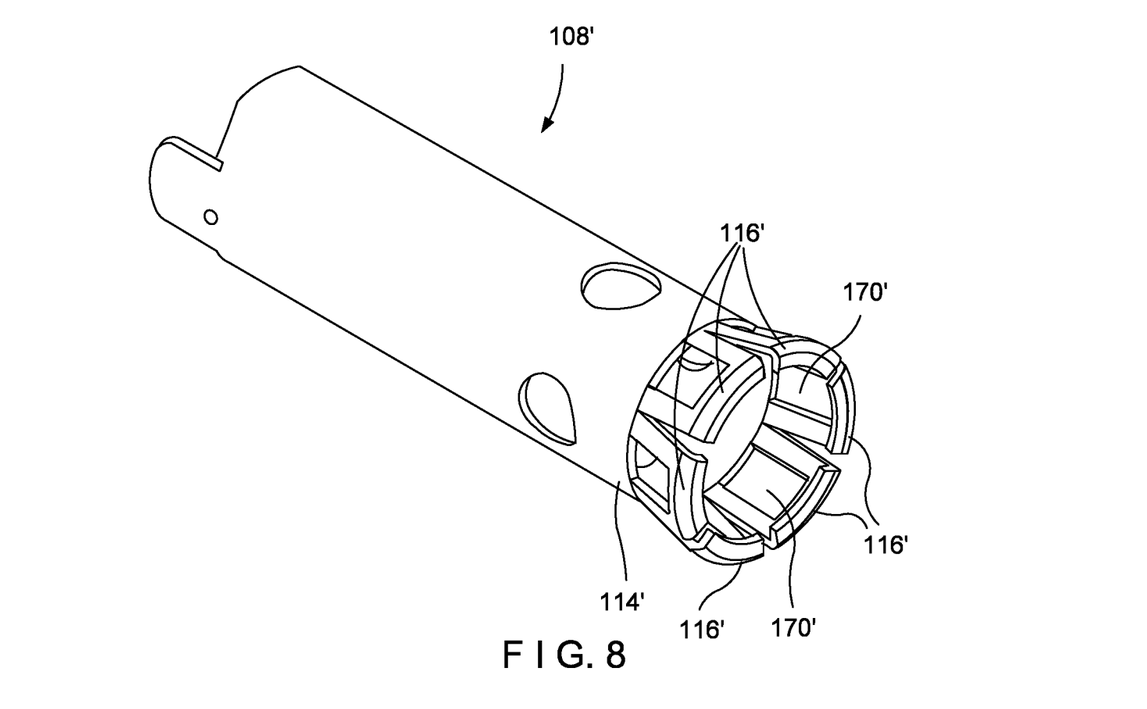
FIG. 8 shows a perspective view of an alternate embodiment of a capsule for the system according to FIG. 1.

In one embodiment, the connecting tabs 116 are formed of a metal selected to permit the slight elastic deformation thereof required during loading of the clip 102 onto the applicator 104 and which will plastically deform during deployment of the clip 102. For example, the connecting tabs 116 may be formed of a stainless steel such as a 300 series stainless steel. In one embodiment, the entire capsule 108, including the connecting tabs 116, may be formed of the same material. It will be understood by those of skill in the art that the force required to cause the plastic deformation of the connecting tabs 116 may be controlled by, for example, adjusting the number of connecting tabs 116 and/or adjusting an amount of material used to form the connecting tabs 116. For example, according to another alternate embodiment, as shown in FIG. 8, a capsule 108' may include six connecting tabs 116' at a proximal end 114' of the capsule 108', each of the connecting tabs 116' including windows 170' extending therethrough so that the connecting tabs 116' include less material and will be thus easier to deform outward during deployment than the connecting tabs 116.

Figure 9:
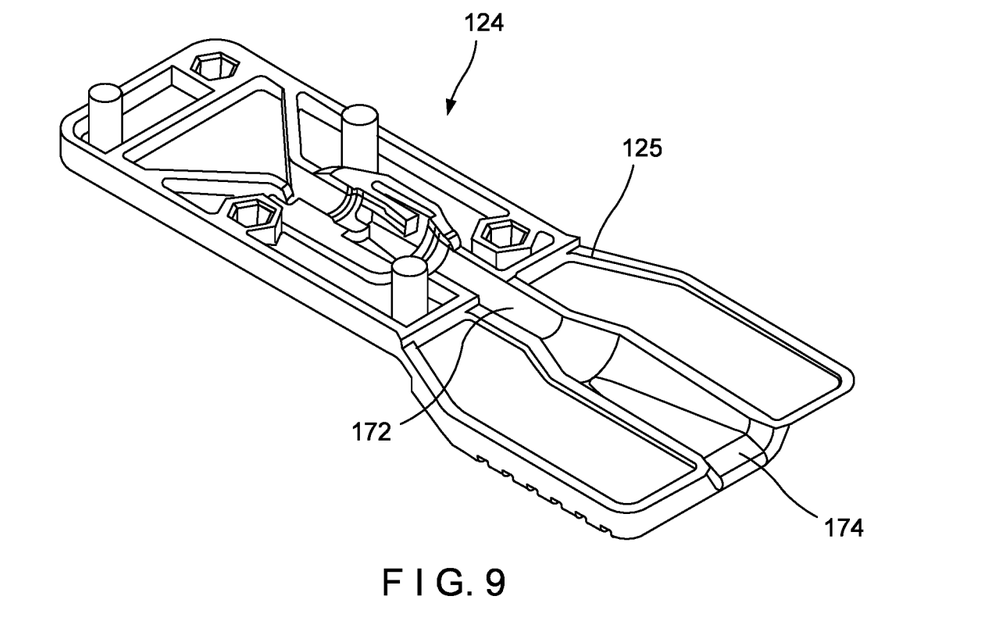
FIG. 9 shows a perspective view of a portion of a cartridge according to the system of FIG. 1.

Prior to being loaded on the applicator 104, the clip 102 may be stored in the cartridge 124, configured to facilitate loading of the clip assembly 102 on the applicator 104. The cartridge 124 may be configured as a storage container including a base 125 and lid (not shown), within which a space 172 sized and shaped to house the clip 102 is defined. In this embodiment, the clip 102 is stored within the cartridge 124 in the open configuration. The cartridge 124 includes a proximal opening 174 through which the distal portion of the applicator 104 may be inserted to be coupled to the clip assembly 102, as will be described in further detail below. The cartridge 124 holds the clip 102 in a position configured to facilitate loading of the clip 102 onto the applicator 104. It should be noted that although FIG. 9 shows only the base 125 of the container 124, an identical lid may be coupled to the base 125 to completely enclose the clip 102.

According to an exemplary method for loading the clip 102 onto the applicator 104, a distal portion of the applicator 104, including the bushing 118, is inserted through the proximal opening 174 of the cartridge 124. The enlarged distal end 122 of the control member 120 is moved distally past the bushing 118 to be inserted distally through the longitudinal slot 136 of the yoke 126 until the enlarged distal end 122 is received within the cavity 134. The bushing 118 is engaged with the capsule 108 by drawing the capsule 108 proximally relative to the bushing 118 (or moving the bushing 118 distally with respect to the capsule 108) so that the engaging elements 148 of the connecting tabs 116 are slid proximally along the first ramped surface 162 of the bushing 118 until the engaging elements 148 are received within the notch 150. Upon loading of the clip 102 onto the applicator 104, the handle portion 154 of the applicator 104 may be used to draw the control member 120 proximally relative to the capsule 108 to move the clip 102 toward the closed configuration. The entire applicator 104 may then be moved proximally relative to the cartridge to draw the clip assembly 102 out of the cartridge, in the closed configuration, via the proximal opening 174.

In use, after the clip 102 has been loaded onto the applicator 104, the clip 102, in the closed configuration, may be inserted into the body to target tissue via, for example, a working channel of an endoscope. Once the clip 102 has reached the target tissue, the clip 102 may be moved toward the open configuration to receive the target tissue between the distal ends 112 of the clip arms 106. The clip 102 may be moved between the open and the closed configurations until the target tissue has been clipped between the clip arms 106, as desired. Once the clip 102 is in the closed configuration clipping the target tissue, as desired, the control member 120 (e.g., via actuators of the handle portion 154) may be moved proximally with respect to the capsule until locking features of the clip arms 106 engage corresponding locking structures of the capsule 108, locking the clip arms 106 relative to the capsule 108 in the closed configuration.

To deploy the clip 102, the control member 120 may be drawn further proximally until the capsule 108 is drawn proximally against the bushing 118 so that the distal end 168 of the second ramped surface 164 exerts a distal force against the engaging elements 148 received within the notch 150. The force against the engaging elements 148 bends the engaging elements 148 against the connecting tabs 116 and the connecting tabs 118 slide proximally along the second ramped surface 164 until the connecting tabs 116 are plastically deformed outward, in a direction away from the longitudinal axis of the capsule 108. Once the connecting tabs 116 have been plastically deformed, the bushing 118 is proximally withdrawn from the capsule 108 leaving the clip 102 in place clipping the target tissue.

The user continues to exert proximal force on the control member 120 until the yoke 126 breaks, fails or otherwise separates at the point 132, releasing the clip arms 106, and thereby the clip 102, from the control member 120 and locking the clip 102 closed over the target tissue. The entire applicator 104, including the control member 120 and the proximal portion 128 of the yoke 126, may then be withdrawn proximally from the body leaving the clip 102 clipped over the target tissue. If so desired, a new clip 102 may be loaded onto the applicator 104, in the same manner as described above, so that the system 100 may then be used to clip a second portion of tissue. This process may be repeated using the same applicator 104 as many times as needed or desired.

Although the capsule 108 of the clip 102 and the bushing 118 of the applicator 104 are described and shown as be coupled via connecting tabs 116 including laterally inwardly extending engaging elements 148 extending from the proximal ends 146 of the connecting tabs 116, it will be understood by those of skill in the art that the connecting tabs 116 of the capsule 108 may have any of a variety of engaging features so long as the capsule 108 is engageable with a corresponding feature of the bushing 118 and is configured to interface with the first and second ramped surfaces 162, 164 of the bushing 118 during a loading and a deployment of the clip 102, respectively, as described above.

Figure 10:
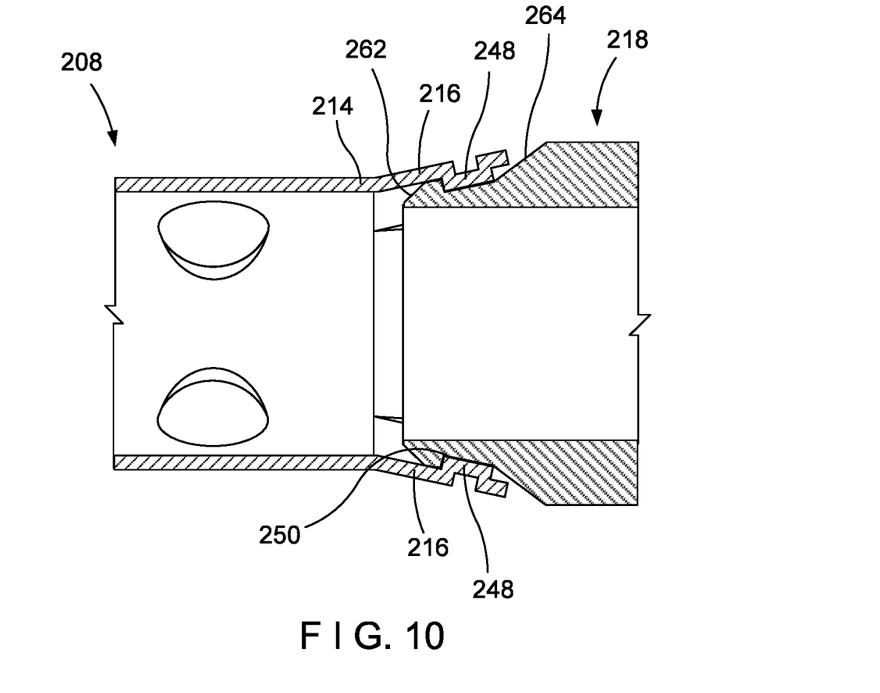
FIG. 10 shows an enlarged longitudinal cross-sectional view of a capsule and bushing according to another exemplary embodiment of the present disclosure.

For example, in another embodiment, as shown in FIG. 10, connecting tabs 216 at a proximal end 214 of a capsule 208 include a stamped boss 248 formed by stamping each of the connecting tabs 216 to include an engaging structure extending inward, toward a longitudinal axis of the capsule 208. The stamped boss 248 is configured to be received within a correspondingly sized and shaped notch 250 extending about a periphery of the bushing 218. Similarly to the system 100 described above, the connecting tabs 216, including the stamped boss 248, slide proximally along a first ramped surface 262 of the bushing 218 until the stamped boss 248 snaps into the notch 250 during a loading of a clip onto an applicator. Similarly to the system 100, during a deployment of a clip, the connecting tabs 216, including the stamped boss 248, are slid proximally along a second ramped surface 264 of the bushing 218 until the connecting tabs 216 are plastically deformed in an outward configuration, in which the connecting tabs 216 are moved in a direction away from the longitudinal axis of the capsule 208.

It will be apparent to those skilled in the art that various modifications may be made in the present disclosure, without departing from the scope of the disclosure.

What is claimed is:

1. A method for treating tissue, comprising:
loading a clip on an applicator by coupling a control member of the applicator to clip arms of the clip and by advancing a bushing distally relative to a proximal end of a capsule of the clip so that a plurality of connecting tabs at the proximal end of the capsule slide along a first ramped surface of the bushing until an engaging feature extending radially inward from a first connecting tab of the connecting tabs engages a corresponding engaging feature of the bushing;
inserting the loaded clip to a target site within a living body via a working channel of an endoscope;
moving the control member distally relative to the capsule to move the clip to an open configuration in which distal ends of the clip arms extend out of the capsule and are separated from one another;
positioning the clip adjacent to a target portion of tissue to be clipped;
moving the control member proximally relative to the capsule to move the clip to a closed configuration in which proximal ends of the clip arms are drawn proximally into the capsule to draw the distal ends of the clip arms toward one another to grip the target portion of tissue;
locking the clip arms relative to the capsule in the closed configuration; and
separating the clip from the applicator by drawing the control member proximally relative to the capsule until the connecting tabs slide proximally along a second ramped surface of the bushing plastically deforming each of the connecting tabs from an initial configuration toward a deployed configuration in which each of the engaging features of the connecting tabs is plastically deformed and bent against the connecting tab from which it extends and the first connecting tab is moved away from a longitudinal axis of the capsule to release the bushing from the capsule.

2. The method of claim 1, wherein the corresponding engaging feature of the bushing is a notch extending about a periphery of the bushing between the first and second ramped surfaces so that the notch defines a proximal end of the first ramped surface and a distal end of the second ramped surface.

3. The method of claim 2, wherein the engaging feature of the first connecting tab includes an engaging element extending radially inward from proximal end of the first connecting tab so that the engaging element of the first connecting tab is received within the notch.

4. The method of claim 3, wherein, during deployment, the distal end of the second ramped surface exerts a distal force on the engaging element, bending the engaging element against the first connecting tab.

5. The method of claim 3, wherein, in the initial configuration, the engaging element extends substantially perpendicular to the longitudinal axis of the capsule.

6. The method of claim 2, wherein the engaging feature of the first connecting tab includes a stamped boss extending along the first connecting tab to be received within the notch extending about a periphery of the bushing.

7. The method of claim 6, wherein the stamped boss extends, in the initial configuration, inward, towards the longitudinal axis of the capsule.

8. The method of claim 2, wherein a diameter of the bushing at the proximal end of the first ramped surface is greater than a diameter of the bushing at the distal end of the second ramped surface.

9. The method of claim 1, wherein each of the first and second ramped surfaces defines a conically shaped portion of the bushing which tapers toward a distal end of the bushing.

10. The method of claim 1, wherein the proximal ends of the clip arms are connected to one another via a yoke couplable with an enlarged distal end of the control member.

11. The method of claim 10, wherein the yoke includes a proximal portion and a distal portion connected to one another at a point configured to separate when a predetermined force is exerted thereon.

12. The method of claim 1, wherein each of the connecting tabs includes a window extending therethrough.

13. The method of claim 1, wherein loading the clip on the applicator includes:
inserting the bushing through a proximal opening of a cartridge;
loading the clip onto the applicator;

drawing the control member proximally relative to the capsule to move the clip toward the closed configuration; and moving the applicator proximally relative to the cartridge so that the clip is removed from the cartridge.

14. The method of claim 1, wherein the engaging feature of the first connecting tab is biased radially inwards towards the longitudinal axis of the capsule.

15. The method of claim 1, wherein the connecting tabs elastically deform as the connecting tabs slide along the first ramped surface and the connecting tabs revert to their initial configuration when the connecting tabs engage the corresponding engaging feature of the bushing.

16. The method of claim 1, wherein locking the clip arms includes drawing the control member proximally relative to the capsule until a locking feature of at least one of the clip arms engages a corresponding locking feature of the capsule.

17. The method of claim 16, wherein the locking feature of the at least one of the clip arms is a locking tab on each the at least one of the clip arms and the corresponding locking feature of the capsule is a locking window of the capsule corresponding to the locking tab.

18. The method of claim 1, wherein, after deployment of the clip, the method is repeated by loading a new clip onto the applicator.

* * * * *